United States Patent [19]
Bolich, Jr. et al.

[11] Patent Number: 4,963,348
[45] Date of Patent: Oct. 16, 1990

[54] STYLING AGENTS AND COMPOSITIONS CONTAINING THE SAME

[75] Inventors: Raymond E. Bolich, Jr., Maineville; Peter M. Torgerson, Washington Court House, both of Ohio

[73] Assignee: The Procter & Gamble Company, Cincinnati, Ohio

[21] Appl. No.: 433,409

[22] Filed: Nov. 3, 1989

Related U.S. Application Data

[63] Continuation of Ser. No. 131,954, Dec. 11, 1987, abandoned.

[51] Int. Cl.$^5$ .............................. A61K 7/06; A61K 7/11
[52] U.S. Cl. ................................. 424/71; 424/47; 424/70; 424/81; 424/DIG. 1; 424/DIG. 2; 424/DIG. 13
[58] Field of Search .................. 424/70, 71, 47, 78, 424/81, DIG. 1, DIG. 2; 252/DIG. 13

[56] References Cited

U.S. PATENT DOCUMENTS

| | | | |
|---|---|---|---|
| 2,816,882 | 12/1957 | Schiller | 526/307.7 |
| 3,222,329 | 12/1965 | Grosser et al. | 260/80.5 |
| 3,577,517 | 5/1971 | Kuboti et al. | 424/47 |
| 3,743,715 | 7/1973 | Viout et al. | 424/47 |
| 3,907,984 | 9/1975 | Calvert et al. | 424/47 |
| 4,012,501 | 3/1977 | Farber | 424/47 |
| 4,030,512 | 6/1977 | Papantoniou et al. | 132/7 |
| 4,151,333 | 4/1979 | Lenke et al. | 526/307.7 |
| 4,165,367 | 8/1979 | Chakrabarti | 424/47 |
| 4,196,190 | 4/1980 | Gehman et al. | 424/71 |
| 4,223,009 | 9/1980 | Chakrabarti | 424/47 |
| 4,272,511 | 6/1981 | Papantoniou et al. | 424/47 |
| 4,283,384 | 8/1981 | Jaquet et al. | 424/47 |
| 4,374,825 | 12/1983 | Bolich, Jr. et al. | 424/70 |
| 4,387,090 | 6/1983 | Bolich, Jr. | 424/70 |
| 4,798,721 | 1/1989 | Yahagi et al. | 424/70 |

FOREIGN PATENT DOCUMENTS

| | | | |
|---|---|---|---|
| 60-229909 | 11/1985 | Japan | 526/307.7 |
| 0833995 | 5/1981 | U.S.S.R. | 526/307.7 |
| 467402 | 6/1937 | United Kingdom | 526/307.7 |
| 764409 | 12/1956 | United Kingdom | 526/307.7 |
| 2155788 | 10/1985 | United Kingdom . | |

OTHER PUBLICATIONS

Encyclopedia of Polymer Science and Engineering, vol. 7, pp. 531–544, John Wiley & Sons, 1987.
Technical Leaflet-Luviskol VA Grades, describes commercially available vinylpyrrolidone/vinyl acetate copolymers.
Technical Leaflet-Luviskol VAP Grades, describes commercially available terpolymers containing vinylpyrrolidone/vinyl acetate/vinyl propionate.

Primary Examiner—Merrell C. Cashion, Jr.
Assistant Examiner—Susan S. Rucker
Attorney, Agent, or Firm—David K. Dabbiere; Gretchen R. Hatfield; Steven J. Goldstein

[57] ABSTRACT

The present invention relates to styling agents comprising adhesive copolymers along with a volatile diluent useful in products such as shampoos and conditioners which provide hair styling hold. The monomer components in these copolymers are randomly distributed in the copolymer chain, preferably to form a substantially linear chain. Preferably, at least one of the monomer components is selected from vinyl pyridine, acrylate amides and methacrylate amides and one of the other monomer components is selected from butadiene, isoprene, isobutene, acrylate esters, methacrylate esters, vinyl alkyl ethers, alkyl-substituted butadienes, and chloroprene. These copolymers also have a single glass transition temperature within the temperature range of from about 0° C. to about 150° C. The volatile diluents useful in these styling agents can be hydrocarbons, esters, ethers, amines, alkyl alcohols, or volatile silicon derivatives.

18 Claims, No Drawings

STYLING AGENTS AND COMPOSITIONS CONTAINING THE SAME

This is a continuation of application Ser. No. 131,954, filed on Dec. 11, 1987, now abandoned.

TECHNICAL FIELD

The present invention relates to rinse-off hair care compositions such as shampoos and conditioners containing water-insoluble styling agents.

BACKGROUND OF THE INVENTION

The desire to have hair retain a particular shape or configuration is one shared by many people, men and women alike. Approaches taken can either involve permanent or temporary alteration of the hair. The former involves the use of chemical agents to react with the hair in order to achieve the desired effect. This process can be carried out at either room temperature or elevated temperature.

The temporary set given to hair is, as the term indicates, a temporary arrangement which can later be removed by water or by shampooing. The materials used to provide the set have generally been resins or gums. The temporary set compositions have taken the form of gels, lotions, and sprays, and, in more recent years, the form of an aerosol foam (i.e., a styling mousse). The compositions are most often applied to hair dampened with water; then combed or spread throughout the hair by other means; followed by letting the hair dry or blow drying the hair.

The set given will vary depending on the materials used. Temporary set hair styling products typically utilize adhesive polymers which are ethanol or water-soluble rigid polymers having glass transition temperatures well above the temperatures experienced in styling hair. Examples of such high glass transition temperature adhesive polymers are found in Viout and Papantoniou U.S. Pat. No. 3,743,715, issued July 3, 1973; Chakrabarti U.S. Pat. No. 4,165,367, issued Aug. 21, 1979; and Chakrabarti U.S. Pat. No. 4,223,009, issued Sept. 16, 1980; the disclosures of all these patents being incorporated herein by reference in their entirety. These adhesive polymers are typically applied to the hair in an ethanol or water solvent, and then set to form rigid welds between hair fibers when the solvent evaporates as the hair dries. These hair fiber welds form the basis for the style hold ability of conventional hair styling products. When these welds are broken, they remain broken unless the appropriate polymer solvent is added to redissolve the adhesive and reform the welds when the hair dries.

In addition, many polymers said to be useful in hair styling products are multi-component polymers which combine three, four, and even more monomers into the polymer chains. Frequently, one of the monomer components is vinyl pyrrolidone. Examples of such complex polymer systems are found in Grosser et al., U.S. Pat. No. 3,222,329, et al., issued Dec. 7, 1965; Kubot et al., U.S. Pat. No. 3,577,517 issued May 4, 1971; Farber U.S. Pat. No. 4,012,501, issued Mar. 15, 1977; Papantoniou and Mondet U.S. Pat. No. 4,272,511, issued June 9, 1981; the disclosures of all these patents being incorporated herein by reference in their entirety.

Other polymers said to be useful for hair styling compositions have been disclosed, such as block polymers. These block polymers have two or more glass transition temperatures. Examples of such block polymer systems are found in Calvert et. al., U.S. Pat. No. 3,907,984, issued Sept. 23, 1975; Papantonious et al., U.S. Pat. No. 4,030,512, issued June 21, 1977; and Jacquet et. al., U.S. Pat. No. 4,283,384, issued Aug. 11, 1981; the disclosures of all these patents being incorporated herein by reference in their entirety.

Notwithstanding the great effort already put forth to identify these adhesive polymers for use in temporary set hair styling products, there remains a continuing need to identify new agents which are useful to provide temporary set and other desirable properties to hair. The styling agents of the present invention contain copolymers of two or more monomer components randomly distributed in the copolymer chain along with a volatile diluent. These copolymers have a single glass transition temperature within the temperature range at which hair styling products are typically utilized (i.e., about 0° C. to about 150° C.) and have several properties which make them superior to previously disclosed hair styling polymers for application to hair.

Thus, an object of the present invention is to provide styling agents useful for providing temporary set style hold to hair while remaining pliable on the hair. A further object is to provide styling agents which lengthen the time such temporary set style hold is perceived to be acceptable. A further object is to provide styling agents which provide good temporary set hair style retention while allowing the perception of continued naturalness such as good hair movement and good hair feel. A further object is to provide styling agents which do not make hair feel stiff or sticky. A further object of the present invention is to provide styling agents which give body and/or fullness to hair, and/or which give the ability to provide lift to hair, and/or which increase hair volume. Finally, an object of the present invention is to provide superior rinse-off hair styling compositions comprising the styling agents of the present invention; and to provide an improved method for styling hair by utilizing a hair styling composition of the present invention.

These and other objects of the present invention will become readily apparent from the detailed description which follows.

All percentages and ratios used herein are by weight unless otherwise specified.

SUMMARY OF THE INVENTION

The present invention relates to styling agents comprising one or more adhesive copolymers along with a volatile diluent which are particularly useful in rinse-off hair styling products. These copolymers comprise two or more monomers which are randomly distributed in a copolymer chain (preferably a substantially linear copolymer chain) such that the copolymer has a single glass transition within the temperature range of from about 0° C. to about 150° C., preferably from about 0°. C. to about 80° C., more preferably from about 20° C. to about 75° C. and most preferably from about 30° C. to about 60° C. Preferably, at least one of the monomer components is selected from vinylpyridine, acrylate amides, and methacrylate amides and at least one of the other monomer components is selected from butadiene, isoprene, isobutene, acrylate esters, methacrylate esters, vinyl alkyl ethers, alkyl-substituted butadienes and chloroprene, and aromatic or alkyl vinyl monomers.

The present invention further relates to hair styling compositions comprising from about 0.5% to about 25% of the styling agent of the present invention, and from about 75% to about 99.5% of a carrier suitable for applying the adhesive copolymer to hair.

Finally, the present invention relates to methods for providing style hold to hair, said method comprising applying to hair in need of style hold an effective amount of a rinse-off hair care composition of the present invention.

DETAILED DESCRIPTION OF THE INVENTION

Water-Insoluble Styling Active

A. Adhesive Copolymers:

An adhesive copolymer of the present invention comprises two or more monomers randomly distributed in a copolymer chain (preferably a substantially linear copolymer chain, i.e., having little or no cross-linking or branching of the copolymer chains) such that the copolymer has a single glass transition temperature within the temperature range of from about 0° C. to about 150° C., preferably from about 0° C. to about 80° C., more preferably from about 20° C. to about 75° C., and most preferably from about 30° C. to about 60° C.

The monomers to be used for synthesizing the copolymers of the present invention are readily chosen from the groups provided hereinafter based on the hydrophobicity of the monomer and the glass transition temperature of a homopolymer of the monomer. Since the copolymers of the present invention have two or more component monomers, one or more of the component monomers will be such that it forms a homopolymer having a glass transition temperature above the temperature desired for the copolymer to be synthesized; and one or more of the other component monomers will be such that it forms a homopolymer having a glass transition temperature below the desired glass transition temperature. Combining these monomers randomly in various weight ratios gives copolymers which have single glass transition temperatures between the higher and lower glass transition temperatures for the homopolymers of the monomers utilized.

Thus, simple manipulation of the weight ratios of the monomers during synthesis of the copolymers and appropriate selection of the relative hydrophilicity/hydrophobicity of the monomers utilized, followed by analysis of the resulting copolymers' single glass transition temperatures, permits easy synthesis of copolymers useful in the present invention having the desired combination of single glass transition temperature and solubility.

Monomers which are to be utilized in the present copolymers and which have glass transition temperatures for their homopolymers above and below the desired single glass transition temperature range for the copolymers of the present invention are known, having been disclosed, for example, in Calvert et al., U.S. Pat. No. 3,907,984 issued Sept. 23, 1975 and incorporated herein by reference in its entirety. Representative monomers having homopolymers with relatively high glass transition temperatures are vinylpyridine (such as 2-vinylpyridine, 4-vinylpyridine, and 2-methyl-5-vinylpyridine); and acrylate amides and methacrylate amides which are preferably unsubstituted or substituted with one or two $C_1$-$C_5$ alkyl groups (i.e., the monomer having the general structure $CH_2=CR(CONR^1R^2)$, wherein R is H or $CH_3$, $R^1$ is H or $C_1$-$C_5$ alkyl, and $R^2$ is H or $C_1$-$C_5$ alkyl). Representative monomers having homopolymers with relatively low glass transition temperatures are vinyl esters, vinyl alkanes, butadiene; isoprene; isobutene; acrylate esters and methacrylate esters which are preferably $C_1$-$C_{15}$ esters of acrylate and methacrylate; vinyl alkyl ethers, which are preferably vinyl $C_1$-$C_5$ alkyl ethers; alkyl-substituted butadienes which are preferably $C_1$-$C_5$ alkyl-substituted butadienes; and chloroprene.

The polymers are selected such that they will dissolve in the water-insoluble diluent and will be soluble at less than 0.1% in water.

Preferably, for the copolymers of the present invention, one monomer component is relatively hydrophilic. Preferred relatively hydrophilic monomer component for use in the copolymers of the present invention are acrylate amides and methacrylate amides, for example, acrylamide, methacrylamide, N-isopropylacrylamide, and especially N,N-dimethylacrylamide. Preferred monomer components which have relatively less hydrophilicity are acrylate esters and methacrylate esters, such as, for example, methylacrylate, ethylacrylate, propylacrylate, butylacrylate, butylmethacrylate, methylmethacrylate, ethylmethacrylate, propylmethacrylate, 2-ethylhexylacrylate, 2-ethylhexyl methacrylate, laurylacrylate, laurylmethacrylate, isobutylacrylate, isobutyl methacrylate, cyclohexylacrylate, and cyclohexylmethacrylate.

Generally, the preferred adhesive copolymers of the present invention are random copolymers having the general structure:

$$(H_x)_m (L_y)_n$$

wherein H is one or more monomer components having homopolymers with relatively high glass transition temperatures such as those described hereinbefore; L is one or more monomer components having homopolymers with relatively low glass transition temperatures such as those described hereinbefore; x is the number of different H monomer components present in the copolymer chain, with x being an integer of 1 or greater (preferably x is 1 or 2; most preferably x is 1); y is the number of different L monomer components present in the copolymer chain, with y being an integer of 1 or greater (preferably y is 1 or 2; most preferably y is 2); the sum of x +y is 2 or greater (preferred is x +y being 3); and m:n is the weight ratio of the H monomer components to L monomer components, and is generally within the range of from about 10:1 to about 1:10 (preferably from about 5:1 to about 1:5).

The preferred L monomer components are selected from acrylate esters and methacrylate esters. Preferred acrylate esters and methacrylate esters are the $C_1$-$C_{15}$ esters of acrylate and methacrylate, for example, methylacrylate, ethylacrylate, propylacrylate, butylacrylate, butylmethacrylate, methylmethacrylate, ethylmethacrylate, 2-ethylhexylacrylate, laurylacrylate, and laurylmethacrylate. More preferred L monomer components are isobutylmethacrylate and 2-ethylhexylmethacrylate.

The preferred H monomer components are selected from acrylate amides and methacrylate amides. Preferred are amides of acrylate and methacrylate in which the nitrogen atom is unsubstituted, or substituted with one or two $C_1$-$C_5$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide.

The most preferred adhesive copolymers of the present invention are random copolymers comprising N,N-dimethylacrylamide and two or more acrylate or methacrylate esters having the general structure:

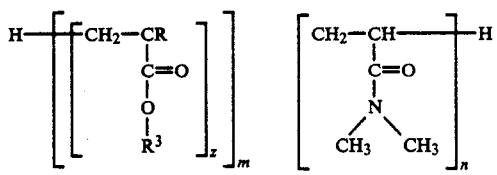

wherein z is the number of different acrylate and methacrylate ester monomer components present in the copolymer chain, with z being an integer of 2 or greater (preferably z=2); the ratio of m:n is within the range of from about 20:1 to about 1:2 (preferably from about 10:1 to about 1:1; more preferably from about 10:1 to about 2:1); R is selected from hydrogen or methyl (preferably R is methyl); and $R^3$ is $C_1$-$C_{15}$ alkyl (preferably $C_1$-$C_{10}$ alkyl). More preferred $R^3$ groups are selected from methyl, ethyl, propyl, butyl, pentyl, and branched alkyl side chains such as isobutyl and 2-ethylhexyl, with most preferred $R^3$ being isobutyl and 2-ethylhexyl.

The term "alkyl", as used herein, means a straight, branched or cyclic carbon-containing chain which is saturated or unsaturated (e.g., one double bond; one triple bond), and which is unsubstituted or substituted with one or more substituent selected from hydroxy, methoxy, ethoxy, propoxy, butoxy, and halogen. Preferred are straight or branched chain, saturated alkyl groups which are unsubstituted.

Also preferred is that the adhesive copolymers of the present invention have a number average molecular weight within the range of from about 10,000 to about 1,000,000, more preferably within the range of from about 10,000 to about 150,000, and most preferably from about 25,000 to about 75,000. It is further preferred that the adhesive copolymers of the present invention have a molecular weight polydispersity (i.e., the ratio of the weight average molecular weight over the number average molecular weight) of about 2.5 or less, preferably from about 2.5 to about 1.0. The adhesive copolymers of the present invention also preferably have an elastic modulus greater than about $10^7$ dynes/cm$^2$, more preferably from about $10^7$ to about $10^{10}$ dynes/cm$^2$, below the copolymer's glass transition temperature.

Analytical methods for analysis of the copolymers of the present invention for their glass transition temperature, numberaverage molecular weights, molecular weight polydispersity, and elastic modulus are well known in the art. For example, these properties of copolymers and analytical methods are described in more detail in Rosen, *Fundamental Principles of Polymeric Materials* (John Wiley & Son, Inc.; New York; 1982), the disclosures of which are incorporated herein by reference in their entirety.

Synthetic methods for preparing random copolymers having substantially linear chains are well known in the art, for example, Grosser, et al., U.S. Pat. No. 3,222,329, issued Dec. 7, 1965; Kubot, et al., U.S. Pat. No. 3,577,517, issued May 4, 1971; Papantoniou and Mondet U.S. Pat. No. 4,272,511, issued June 9, 1981; and Farber U.S. Pat. No. 4,012,501, issued Mar. 15, 1977; the disclosures of all these patents being incorporated herein by reference in their entirely. Preferably, the copolymers of the present invention are prepared by utilizing free radical polymerization techniques. Typically, such free radical polymerization techniques use either UV wavelength light or chemicals which generate free radicals to initiate the polymerization reaction. Representative procedures for synthesizing low glass transition temperature cationic or nonionic adhesive copolymers of the present invention are provided in the examples hereinafter.

B. Volatile Diluent:

The volatile diluents useful in the present compositions can be hydrocarbons, esters, ethers, amines, alkyl alcohols or silicon derivatives or mixtures thereof and have a boiling point in the range of from about 99° C. to about 260° C. and have a solubility in water of less than about 0.2%. Preferably the volatile diluent is selected from the group of alkyl alcohols and silicon derivatives and mixtures thereof.

The hydrocarbons may be either straight or branched chain and may contain from about 10 to about 16, preferably from about 12 to about 16 carbon atoms. Examples of suitable hydrocarbons are decane, dodecane, decene, tridecane and mixtures thereof. Also useful are the terpenes such as orange and lemon terpenes. Useful alkyl alcohols can be saturated or unsaturated and branched or straight chain. Preferred alkyl alcohols include linalool and decyl alcohol.

The volatile silicon derivatives useful in the compositions of the present invention may be either a cyclic or a linear polydialkylsiloxane, linear siloxy compounds or silane. The number of silicon atoms in the cyclic silicones is preferably from about 3 to about 7, more preferably about 3 to about 5.

The general formula for such silicones is:

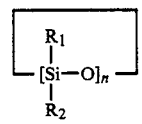

wherein $R_1$ and $R_2$ are independently selected from $C_1$ to $C_8$ alkyl, aryl or alkylaryl and wherein n=3-7. The linear polyorgano siloxanes have from about 2 to 7 silicon atoms and have the general formula:

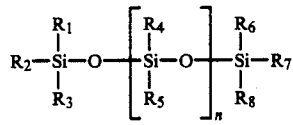

wherein $R_1$, $R_2$, $R_3$, $R_4$, $R_5$, $R_6$, $R_7$, and $R_8$ can independently be saturated or unsaturated $C_1$-$C_8$ alkyl, aryl, alkyl aryl, hydroxyalkyl, amino alkyl or alkyl siloxy.

Linear siloxy compounds have the general formula:

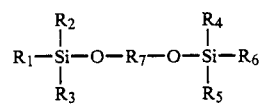

wherein $R_1$, $R_2$, $R_3$, $R_4$, $R_5$ and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

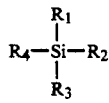

wherein $R_1$, $R_2$, $R_3$, and $R_4$ can independently be selected from $C_1$-$C_8$ alkyl, aryl, alkyl aryl, hydroxy alkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. "Volatile" means that the material has a measurable vapor pressure.

A description of volatile silicones is found in Todd and Byers, "Volatile Silicone Fluids for Cosmetics", Cosmetics and Toiletries, Vol. 91, January, 1976, pp. 27–32, and also in Silicon Compounds, pages 253–295, distributed by Petrarch Chemicals, both of which are incorporated herein by reference.

Optionally, certain water-insoluble non-volatile co-solvents can be added at low levels, i.e., less than about 10%, to replace a similar amount of the volatile diluents. These co-solvents help to dissolve the adhesive copolymer. Preferred co-solvents include liquid alcohols and liquid fatty acids such as isocetyl alcohol and olelyl alcohol.

In order to form the styling agent, the adhesive copolymer and the volatile diluent are combined in a weight ratio of from about 1:20 to about 5:1, preferably from about 1:10 to about 1:1 and most preferably from about 1:4 to about 2:3, the resulting styling agents have an average particle diameter of from about 0.5 to about 100 microns, preferably from about 1 micron to about 25 microns.

Carriers Suitable for Applying Styling Agents to Hair

The hair styling compositions of the present invention contain the hair styling agents described above along with a carrier suitable for applying the styling agent to hair. These compositions are of two or more phases; at least one containing the styling agent and another containing the carrier. Other phases can contain, for example, pearlizing agents such as ethylene glycol distearate or $TiO_2$ coated mica which impart aesthetic benefits to the composition. The term "carriers suitable for applying the styling agent to hair", as used herein, means one or more compatible water-based vehicles which are suitable for adminstration to the hair of a human or lower animal. The term "compatible", as used herein, means that the components of the carrier are capable of being commingled with the adhesive copolymer of the present invention, and with each other, in a manner such that there is no interaction which would substantially reduce the ability of the hair styling compositions to provide temporary set hold to hair under ordinary use situation. These carriers must, of course, be of sufficiently high purity and sufficiently low toxicity to render them suitable for administration to the hair of the human or lower animal to which they are being applied.

Carriers suitable for applying the styling agents such as shampoos and cream rinse conditioners to hair are well known in the art; and their selection can be made without difficulty by a person skilled in the art. For example, carriers which may be selected for use in the hair styling compositions of the present invention are described in more detail in Kubot et al, U.S. Pat. No. 3,577,517, issued May 4, 1971; Calvert et al, U.S. Pat. 3,907,984, issued Sept. 23, 1975; Farber U.S. Pat. No. 4,012,501, issued Mar. 15, 1977; Chakrabarti U.S. Pat. No. 4,223,009, issued Sept. 16, 1980; and Jacquet et al, U.S. Pat. No. 4,283,384, issued Aug. 11, 1981; the disclosures of all these patents being incorporated herein by reference in their entirety.

The rinse-off hair styling compositions of the present invention typically comprise water (preferably distilled or deionized), or a water-alcohol mixture (typically in a water:alcohol ratio within the range of from about 20:1 to about 1:2), as part of the carrier. The carrier is present at a level of from about 75% to about 99.5%, preferably from about 85% to about 99%,1 and most preferably from about 90% to about 99% of the total hair styling composition.

Compositions of this invention also can be formulated in a shampoo form. The shampoos comprise from about 1% to about 25% of the styling agent; from about 5% to about 60% of a synthetic surfactant; and the balance water. Suitable surfactants which have been fully described above include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate.

These shampoos can contain a variety of nonessential optional components. Such conventional optional ingredients are well known to those skilled in the art, e.g., preservatives, such as benzyl alcohol, ethyl paraben, propyl paraben and imidazolidinyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as a diethanolamide of a long-chain fatty acid (e.g. PEG 3 lauramide), block polymers of ethylene oxide and propylene oxide, sodium chloride, sodium sulfate, polyvinyl alcohol, ethyl alcohol and water-soluble polymers such as xanthan gum, hydroxyethyl cellulose, guar gum and starch; pH adjusting agents, such as citric acid, succinic acid, phosphoric acid, sodium hydroxide, sodium carbonate; perfumes; dyes; and, sequestering agents, such as disodium ethylenediamine tetraacetate. Such agents generally are used individually at a level of from about 0.01% to about 10%, preferably from about 0.5% to about 5.0% by weight of the composition.

Where the hair styling compositions are conditioner compositions, preferred optional components include gel vehicle materials. The vehicle preferably comprises two essential components: a lipid vehicle material and generally a cationic surfactant vehicle material. Such gel-type vehicle are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000 –Cetostearyl Alcohol, I. Self Bodying Action", 38 *J. of Colloid and Interface Science* 616–625 (1972).

Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3d edition, Swern, ed. 1979) (incorporated by reference herein). Fatty alcohols included among those useful herein are disclosed in the following documents, all incorporated by reference herein: Hilfer U.S. Pat. No. 3,155,591, issued Nov. 3, 1964; Watanabe, et al., U.S. Pat. No. 4,165,369, issued Aug. 21, 1979; Villamarin, et al., U.S. Pat. No. 4,269,824, issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–102 (1983). Fatty esters included among those useful herein are disclosed in Kaufman, et al., U.S. Pat. No. 3,341,465, issued Sept. 12, 1967 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Other carrier components useful in the hair styling compositions of the present invention are suitable for rendering such compositions more acceptable. These include conventional additives such as opacifiers, colorants, perfumes, UV absorbers, preservatives, medicaments, suds boosters or depressants, penetrants, lustrants, deodorants, and the like. Such carriers are described in more detail in Chakrabarti U.S. Pat. No. 4,223,009, issued Sept. 16, 1980, and in Jacquet et al U.S. Pat. No. 4,283,384, issued Aug. 11, 1981, the disclosures of both these patents being incorporated by reference herein in their entirety.

The hair styling compositions of the present invention typically comprise from about 80% to about 99.9% of a carrier suitable for applying the adhesive copolymer to hair, preferably from about 90% to about 99%, and most preferably from about 95% to about 99%.

Methods for Providing Styling Hold to Hair:

Another aspect of the present invention is methods for providing temporary set style hold to hair. Such methods comprise applying to the hair in need of style hold an effective amount of styling agent or hair styling composition of the present invention.

The procedure for applying the styling agent to the hair will vary according to the form of the hair styling composition being utilized. For example, hair styling compositions in the form of a shampoo or conditioner lotion are typically applied to the hair when wet, with the hair then being rinsed and dried. An effective amount of the styling agent or composition of the present invention is considered to be an amount sufficient to provide the degree of styling hold desired by the user.

The following examples further describe and demonstrate the preferred embodiments within the scope of the present invention. The examples are given solely for the purpose of illustration and are not to be construed as limitation of the present invention as many variations thereof are possible without departing from spirit and scope.

EXAMPLES

The following examples illustrate the present invention. The following adhesive copolymers are used in the examples.

STYLING POLYMER A

Isobutylmethacrylate/2-ethylhexylmethacrylate/N,N-dimethylacryla-mide (60:30:10) copolymer A 60:30:10 (weight percent) isobutylmethacrylate/2-ethyl-hexylmethacrylate/N,N-dimethylacrylamide copolymer is prepared as follows. Isobutylmethacrylate, 2-ethylhexylmethacrylate, and N,N-dimethylacrylamide are weighed out (relative weight ratios of 60:30:10) and added to a four neck flask fitted with an argon sparge, mechanical stirrer, thermometer and condenser. Toluene is then added to the flask to get a final monomer concentration of 25.0 weight percent. The reaction flask is placed in a 60° C. water bath and the reaction mixture is sparged with argon for two hours while stirring. After two hours, azobisisobutyronitrile ("AIBN") is added to the reaction flask in an amount sufficient to get a final initiator concentration of 0.25 weight percent. The reaction is then stirred for two hours, after which time the reaction flask is removed from the water bath and the reaction mixture is poured into a polyethylene tray, air dried, and dried in a vacuum oven at 120° C. Optionally, after two hours of stirring, an additional 0.25% initiator is added and the reaction continued for an additional hour. It is then dried as stated. If it is desired to increase or decrease the polymer molecular weight this is done by altering the level of initiator used, or by adding a chain transfer agent (such as decanethiol) to the reaction mixture. The glass transition temperature of this copolymer is calculated to be approximately 38° C.

STYLING POLYMER B

Isobutylmethacrylate/2-ethylhexylmethacrylate/N,N-dimethyl-acrylamide (30:40:30) copolymer An isobutylmethacrylate/2-ethylhexylmethacrylate/N,N-dimethylacrylamide copolymer having monomer content in a weight ratio of 30:40:30 is prepared by following essentially the same procedure as described above. The glass transition temperature is calculated to be approximately 44° C.

STYLING POLYMER C

Butylmethacrylate/N,N-dimethylacrylamide (80:20) copolymer

A butylmethacrylate/N,N-dimethylacrylamide copolymer having monomer content in a weight ratio of 80:20 is prepared by following essentially the same procedure as described above. The glass transition temperature is calculated to be approximately 30° C.

EXAMPLE I

A shampoo composition of the present invention is made by combining the following components.

| Component | Weight % |
| --- | --- |
| Styling Agent | |
| Copolymer C | 02.00 |
| Orange terpenes | 06.00 |
| Main Mix | |
| Ammonium lauryl sulfate | 15.00 |
| Jaguar HOP-60[1] | 01.00 |
| Kathon CG[2] | 00.03 |
| Perfume | 00.20 |
| DRO H$_2$O[3] | q.s |

[1]Hydroxypropyl guar gum offered by Hi-tek polymers, Inc.
[2]Preservative offered by Rohm and Haas
[3]Double reverse osmosis water The styling agent (premix) is preblended in a conventional manner known to one skilled in the art. The resulting premix resembles an oil. The premix is then dispersed into the main mix by conventional methods including low shear operations such as a propellar stirrer as well as high shear methods such as colloidal milling.

EXAMPLE II

A Shampoo Composition is made by combining the following components.

| Component | Weight % |
| --- | --- |
| Styling Agent | |
| Copolymer A | 01.00 |
| 1-decene | 02.00 |
| Main Mix | |
| Ammonium lauryl sulfate | 10.00 |
| Ammonium laureth sulfate | 06.00 |
| Ethylene glycol distearate | 03.00 |
| Cocamide MEA | 01.00 |
| Kathon CG | 00.03 |
| DRO H$_2$O | q.s |

EXAMPLE III

A Shampoo Composition is made by combining the following components.

| Component | Weight % |
| --- | --- |
| Styling Agent | |
| Copolymer B | 03.00 |
| Cyclomethicone (tetramer) | 09.00 |
| Decyl alcohol | 03.00 |
| Main Mix | |
| Ammonium lauryl sulfate | 11.00 |
| Cocamidopropyl betaine | 04.00 |
| Jaguar HP 60 | 01.10 |
| Kathon CG | 00.03 |
| DRO H$_2$O | q.s. |

EXAMPLE IV

A Shampoo Composition is made by combining the following components.

| Component | Weight % |
| --- | --- |
| Styling Agent | |
| Copolymer A | 00.50 |
| Cyclomethicone (tetramer) | 00.80 |
| Decyl alcohol | 00.20 |
| Premix | |
| Silicone gum[1] | 00.50 |
| Cyclomethicone (tetramer) | 00.60 |
| Main Mix | |
| Ammonium lauryl sulfate | 11.00 |
| Cocamide MEA | 01.50 |
| Xanthan gum | 01.20 |
| Kathon CG | 00.03 |
| DRO H$_2$O | q.s. |

[1]G.E. Sillicone gum SE-76 offered by General Electric

The styling agent and premix are blended separately and combined with the other ingredients as described above in Example I.

EXAMPLE V

A Styling Rinse Composition is made by combining the following components.

| Component | Weight % |
| --- | --- |
| Styling Agent | |
| Copolymer A | 02.00 |
| 1-decene | 06.00 |
| Main Mix | |
| Veegum[1] | 01.40 |
| Xanthan gum | 01.40 |
| Cyclomethicone (tetramer) | 00.90 |
| Silicone gum[2] | 00.30 |
| Decyl alcohol | 00.80 |
| Kathon CG | 00.03 |
| DRO H$_2$O | q.s. |

[1]Magnesium aluminum silicate offered by R. T. Vanderbilt Co.
[2]G.E.S.E. 76

EXAMPLE VI

A Conditioner Composition is made by combining the following components.

| Component | Weight % |
| --- | --- |
| Styling Agent | |
| Copolymer A | 3.00 |
| Phenyl pentamethyl disiloxane | 9.00 |
| Premix | |
| Silicone gum[4] | 0.10 |
| Cyclomethicone (pentamer) | 0.50 |
| Main Mix | |
| Distearyl dimethyl ammonium chloride | 0.85 |
| Natrosol 250M[1] | 0.50 |
| Dow Corning 190[2] | 0.10 |
| Cetyl alcohol | 1.00 |
| Stearyl alcohol | 1.00 |
| Cetareth-20 | 0.35 |
| Lexamine S-13[3] | 0.50 |
| Perfume | 0.10 |
| Kathon CG | 0.03 |

| Component | Weight % |
| --- | --- |
| DRO H₂O | q.s. |

[1] Hydroxyethylcellulose offered by Hercules, Inc.
[2] A silicone copolyol offered by Dow Corning Corp.
[3] a fatty amine offered by Inolex Chemical Division of American Can Company
[4] G.E.S.E. 76

EXAMPLE VII

A Conditioner Composition is made by combining the following components.

| Component | Weight % |
| --- | --- |
| Styling Agent | |
| Copolymer A | 0.80 |
| Hexaethyl disiloxane[1] | 2.00 |
| Isocetyl alcohol | 0.05 |
| Main Mix | |
| Stearalkonium chloride | 1.00 |
| Cetrimonium chloride | 0.50 |
| Cetyl alcohol | 1.20 |
| Stearyl alcohol | 0.50 |
| Ceteth-2 | 1.00 |
| Glyceryl monostearate | 0.50 |
| Sodium chloride | 0.05 |
| Kathon CG | 0.03 |
| DRO H₂O | q.s. |

[1] Supplied by Petrarch Chemical

EXAMPLE VIII

A Conditioner Composition is made by combining the following components.

| Component | Weight % |
| --- | --- |
| Styling Agent | |
| Copolymer B | 3.00 |
| D₄ cyclomethicone | 6.75 |
| Linalool | 2.25 |
| Premix | |
| D₅ cyclomethicone | 1.70 |
| Silicone gum[1] | 0.30 |
| Main Mix | |
| Dow Corning 190 silicone surfactant | 0.50 |
| Cetyl alcohol | 0.99 |
| Stearyl alcohol | 0.66 |
| Lexamine S-13[2] | 0.50 |
| Ceteareth-20 | 0.13 |
| Glycerol monostearate | 0.25 |
| Fragrance | 0.25 |
| Citric acid | 0.09 |
| Kathon CG[3] | 0.04 |
| DRO water | q.s. |

[1] G.E.S.E. 76
[2] Offered by Inolex Chemical Division of American Can Co.
[3] Offered by Rohm and Haas Company, Inc.

EXAMPLE IX

A Tonic Composition is made by combining the following components.

| Component | Weight % |
| --- | --- |
| Styling Agent | |
| Copolymer A | 0.30 |
| Phenyl pentamethyl disiloxane | 1.00 |
| Main Mix | |
| Ethanol, SDA40 | 5.00 |
| Carbopol 934[1] | 0.30 |
| Sodium hydroxide | 0.15 |

| Component | Weight % |
| --- | --- |
| Preservative | 0.10 |
| DRO H₂O | q.s. |

[1] Offered by B. F. Goodrich Company.

What is claimed is:

1. A styling agent comprising:
   A. an adhesive copolymer having two or more monomers randomly distributed in a substantially linear copolymer chain wherein said copolymer has a single glass transition temperature of from about 0° C. to about 150° C. and a number-average molecular weight of from about 10,000 to about 1,000,000; and wherein said copolymer has a water solubility of less than 0.1% and
   B. a volatile diluent selected from the group consisting of hydrocarbons, esters, ethers, amines, alkyl alcohols and silicon derivatives and mixtures thereof and wherein said diluent has a boiling point of from about 99° C. to about 260° C. and a water solubility of less than about 0.2% at 25° C.;
   wherein said adhesive copolymer is soluble in said volatile diluent, and the weight ratio of adhesive copolymer to volatile diluent is from about 1:20 to about 5:1.

2. A styling agent according to claim 1 wherein the adhesive copolymer has a glass transition temperature of from about 20° C. to about 75° C. and a molecular weight of from about 25,000 to about 75,000.

3. A styling agent according to claim 2 wherein the volatile diluent is selected from the group consisting of hydrocarbons, silicon derivatives and mixtures thereof.

4. A styling agent according to claim 3 wherein the weight ratio of adhesive copolymer to volatile diluent is from about 1:10 to about 1:1 and wherein said styling agent has an average particle diameter of from about 1 micron to about 25 microns.

5. A styling agent comprising:
   A. an adhesive copolymer having two or more monomers randomly distributed in a substantially linear copolymer chain having the general structure

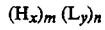

$(H_x)_m (L_y)_n$ wherein:
   (a) the ratio of m:n is within the range of from about 10:1 to about 1:10;
   (b) L is one or more monomer components selected from the group consisting of acrylate esters and methacrylate esters;
   (c) H is one or more monomer components selected from the group consisting of acrylate amides and methacrylate amides; and
   (d) x and y are integers of 1 or greater, and x+y is an integer of 2 or greater;
   and wherein further said adhesive copolymers have a single glass transition temperature within the range of from about 0° C. to about 150° C. and wherein said copolymer has a water solubility of less than 0.1%;
   B. A volatile diluent selected from the group consisting of hydrocarbons, esters, ethers, amines, alkyl alcohols and silicon derivatives and mixtures thereof and wherein said diluent has a boiling point of from about 99° C. to about 260° C. and a water solubility of less than about 0.2% at 25° C.; wherein said adhesive copolymer is soluble in said volatile diluent, and the weight ratio of adhesive copolymer to volatile diluent is from about 1:20 to about 5:1.

6. A styling agent according to claim 5 wherein the L monomer components of the adhesive copolymer are selected from the group consisting of methylacrylate, ethylacrylate, propylacrylate, butylacrylate, butylmethacrylate, methylmethacrylate, ethylmethacrylate, 2-ethylhexylacrylate, 2-ethylhexylmathacrylate, isobutylacrylate, isobutylmethacrylate, laurylacrylate, laurylmethacrylate cyclohexylacrylate, and cyclohexylmethacrylate; the H monomer components are selected from the group consisting of acrylamide, methacrylamide, N-isopropylacrylamide and N,N-dimethylacrylamide; and x+y=3; and wherein further said adhesive copolymers have a number-average molecular weight in the range of from about 10,000 to about 1,000,000.

7. A styling agent according to claim 6 wherein the ratio of m:n is within the range of from about 5:1 to about 1:5; the L monomer components are selected from isobutylmethacrylate and 2-ethylhexylmethacrylate and mixtures thereof; the H monomer component is N,N-dimethylacrylamide: x is 1; and y is 2.

8. A two or more phase rinse-off hairstyling composition comprising:
A. from about 0.5% to about 25% of a styling agent comprising:
  (i) adhesive copolymer having two or more monomers randomly distributed in a substantially linear copolymer chain wherein, said copolymer has a single glass transition temperature of from about 0° C. to about 150° C., and a number-average molecular weight of from about 10,000 to about 1,000,000, and wherein said copolymer has a water solubility of less than 0.1%; and
  (ii) a volatile diluent selected from the group consisting of hydrocarbons, esters, ethers, amines, alkyl alcohols and silicon derivatives and mixtures thereof and wherein said diluent has a boiling point of from about 99° C. to about 260° C. and a water solubility of less than about 0.2% at 25° C.; and wherein said adhesive copolymer is soluble in said volatile diluent, and
B. from about 75% to about 99.5% of an aqueous carrier.

9. A composition according to claim 8 wherein said diluent is selected from the group consisting of terpenes, decene, cyclomethicone, dodecane, linalool, pentamethyl disiloxane, hexaethyl disiloxane and mixtures thereof.

10. A rinse-off hair styling composition comprising:
A. from about 0.5% to about 25% of a styling active comprising:
  (i) a low glass transition temperature adhesive random copolymer having the general structure:

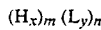

wherein:
  (a) the ratio of m:n is within the range of from about 10:1 to about 1:10;

(b) L is one or more monomer components selected from the group consisting of acrylate esters and methacrylate esters;
  (c) H is one or more monomer components selected from the group consisting of acrylate amides and methacrylate amides; and
  (d) x and y are integers of 1 or greater, and x+y is an integer of 2 or greater;
  and wherein further said random copolymers have a single glass transition temperature of from about 0° C. to about 150° C.; and wherein said copolymer has a water solubility of less than 0.1%
  (ii) a volatile diluent selected from the group consisting of hydrocarbons, esters, ethers, amines, alkyl alcohols and silicon derivatives and mixtures thereof and wherein said diluent has a boiling point of from about 99° C. to about 260° C. and a water solubility of less than about 0.2% at 25° C. and wherein said adhesive copolymer is soluble in said volatile diluent, and
B. from about 75% to about 99.5, of an aqueous carrier.

11. A hairstyling composition according to claim 10 wherein the L monomer components of the adhesive copolymer are selected from the group consisting of methylacrylate, ethylacrylate, propylacrylate, butylacrylate, butylmethacrylate, methylmethacrylate, ethylmethacrylate, 2-ethylhexylacrylate, 2-ethylhexylmathacrylate, isobutylacrylate, isobutylmethacrylate, laurylacrylate, laurylmethacrylate cyclohexylacrylate, and cyclohexylmethacrylate; the H monomer components are selected from the group consisting of acrylamide, methacrylamide, N-isopropylacrylamide and N,N-dimethylacrylamide; and x+y=3; and wherein further said adhesive copolymers have a number-average molecular weight in the range of from about 10,000 to about 1,000,000.

12. A hairstyling composition according to claim 5 wherein the ratio of m:n is within the range of from about 5:1 to about 1:3; the L moiety is selected from isobutylmethacrylate, 2-ethylhexylmethacrylate and mixtures thereof and the H moiety is N,N-dimethylacrylamide.

13. A hairstyling composition according to claim 5 wherein said aqueous carrier is selected from the group consisting of shampoos and creme rinse conditioners.

14. A hair care composition according to claim 13 in the form of a shampoo which in addition contains from about 10% to about 35% of a synthetic surfactant or mixtures thereof.

15. A hair care composition according to claim 14 wherein the synthetic surfactant is selected from the group consisting of alkyl sulfates, ethoxylated alkyl sulfates and mixtures thereof.

16. A hair care composition according to claim 13 in the form of a conditioner which additionally contains from about 0.1% to about 10.0% of a lipid vehicle material and from about 0.05% to about 5.0% of a cationic surfactant.

17. A hair care composition according to claim 16 wherein the cationic surfactant is a quaternary ammonium salt.

18. A hair care compostion according to claim 17 wherein the lipid vehicle material is selected from the group consisting of cetyl alcohol, stearyl alcohol, cetyl palmitate, glyceryl monostearate and mixtures thereof.

* * * * *